United States Patent [19]

Meek et al.

[11] Plant 4,692

[45] Apr. 14, 1981

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 100,116

[22] Filed: Dec. 4, 1979

[51] Int. Cl.[3] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar particularly characterized as to uniqueness by the combined characteristics of flat capitulum form; daisy capitulum type; light lavender pink ray floret color with minimum color oxidation; yellow-green (immature) to yellow (mature) disc floret color; diameter across face of capitulum ranging from 75 to 95 mm. at maturity; uniform nine week photoperiodic flowering response to short days; tall plant height when grown as a single stem cut spray; medium peduncle length; and semi-upright branching pattern.

3 Drawing Figures

1

The present invention comprises a new and distinct cultivar of *Chrysanthemum morifolium,* Ramat., hereinafter referred to by the cultivar name Nova.

Nova is an induced mutation of an unnamed light pink seedling daisy and was selected to intensify the color of the parental variety. The parental seedling of Nova was a product of a planned breeding program which had the objective of creating new chrysanthemum cultivars with daisy capitulum type, lavender pink ray floret color, nine week flowering response and with the ability to produce commercially acceptable quality in year round cut mum programs. Such traits in combination were not present in previously available commercial cultivars.

Nova was discovered and selected as one flowering plant within a flowering block of the parental seedling by Jack M. Meek and William E. Duffett on Nov. 17, 1977 in a controlled environment in Salinas, Calif. Plants within the flowering block were derived from stock plants which had been irradiated as unrooted cuttings with an x-ray source of 2600 R units.

The first act of asexual reproduction of Nova was accomplished when vegetative cuttings were taken from the initial selection in August, 1978 in a controlled environment in Salinas, Calif. by a technician working under formulations established and supervised by Jack M. Meek and William E. Duffett. Continued asexual reproduction by vegetative cuttings for evaluative tests in flowering and stock programs in conjunction with horticultural examination of selected plants initiated in November, 1978 has demonstrated that the combination of characteristics as herein disclosed for Nova are firmly fixed and are retained through successive generations of asexual reproduction.

Nova has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristcs of Nova

2 which in combination distinguish this chrysanthemum as a new and distinct cultivar:

(1) flat capitulum form, (2) daisy capitulum type, (3) light lavender pink ray floret color with minimum color oxidation, (4) yellow-green (immature) to yellow (mature) disc floret color, (5) diameter across face of capitulum ranging from 75 to 95 mm. at maturity, (6) uniform nine week photoperiodic flowering response to short days, (7) tall plant height (attaining a height as a flowered plant of 75 to 90 cm. from a rooted cutting planted to short days for April through November flowerings), (8) medium peduncle length, and (9) semi-upright branching pattern.

Of the many commercial cultivars known to the present inventors, the most similar in comparison to Nova is Blue Marble (unpatented). Reference is made to attached Chart A which compares certain characteristics of Nova to those same characteristics of Blue Marble. Compared generally to Blue Marble, Nova has different ray floret color, longer ray floret color retention, smaller diameter across face of capitulum, taller plant height and shorter peduncle length. The capitulum form, capitulum type and flowering response period of Blue Marble are similar to those same characteristics of Nova.

The accompanying photographic drawings show typical inflorescence and foliage characteristics of Nova, with the colors being as nearly true as possible with illustrations of this type. Sheet 1 is a color photograph of Nova grown as a single stem cut spray. Sheet 2 is a black and white photograph showing the foliage of Nova at three stages of growth. Sheet 3 is a black and white photograph of three views of the inflorescence of Nova.

In the following description color references are made to A Limit Color Cascade by the Munsell Company, 1972 edition. The color values were determined between 9:30 and 10:00 a.m. on May 10, 1979 under 100 foot-candle light intensity at Salinas, Calif.

Classification:

*Botanical.*—*Chrysanthemum morifolium,* Ramat., cv NOVA.

*Commercial.*—Cut daisy spray.

1. Inflorescence:

A. *Capitulum.*—Form: flat. Type: daisy. Diameter across face: 75 to 95 mm.

B. *Corolla of ray florets.*—General tonality (from a distance of three meters): light lavender pink, approximately 46-3 to 46- 2. Color (abaxial): approximately 46-3 streaked with 46-4 oxidizing to 46-2. Color (adaxial): approximately 46-4 streaked over 46-2.

C. *Corolla of disc florets.*—Color (abaxial): approximately 27-5. Color (adaxial): approximately 22-13 to 22-10.

D. *Reproductive organs.*—Gynoecium: present both ray and disc florets. Androecium: present disc florets only; numerous; scant to no pollen.

II. Plant:

A. *General Appearance.*—Branching pattern: semi-upright. Height: tall, attaining a height of 75 to 90 cm. as a flowered plant from a rooted cutting with no long days for April through November flowerings.

B. *Foliage.*—Color (abaxial): approximately 21-15. Color (adaxial): approximately 21-15 overlaid with white. Shape: deeply lobed and slightly serrated.

CHART A

COMPARISON OF NOVA AND BLUE MARBLE

| Cultivar | Ray Floret Color | Capitulum Form & Type | Diameter Across Face of Capitulum | Plant Height | Flowering Response Period | Peduncle Length |
|---|---|---|---|---|---|---|
| NOVA | Light lavender pink with minimum color oxidation | Flat Daisy | 75 to 95 mm. | Tall 75 to 90 cm. | 9 week | Medium 10 to 15 cm. |
| BLUE MARBLE | Medium lavender pink with rapid oxidation | Flat Daisy | 95 to 105 mm. | Tall 75 to 85 cm. | 9 week | Long 15 to 20 cm. |

We claim:

1. A new and distinct cultivar *Chrysanthemum morifolium,* Ramat., plant known by the cultivar name Nova, as described and illustrated, and particularly characterized as to uniqueness by the combined characteristics of flat capitulum form; daisy capitulum type; light lavender pink ray floret color with minimum color oxidation; yellow green (immature) to yellow (mature) disc floret color; diameter across face of capitulum ranging from 75 to 90 mm. at maturity; uniform nine week photoperiodic flowering response to short days; tall plant height, medium peduncle length; and semi-upright branching pattern.

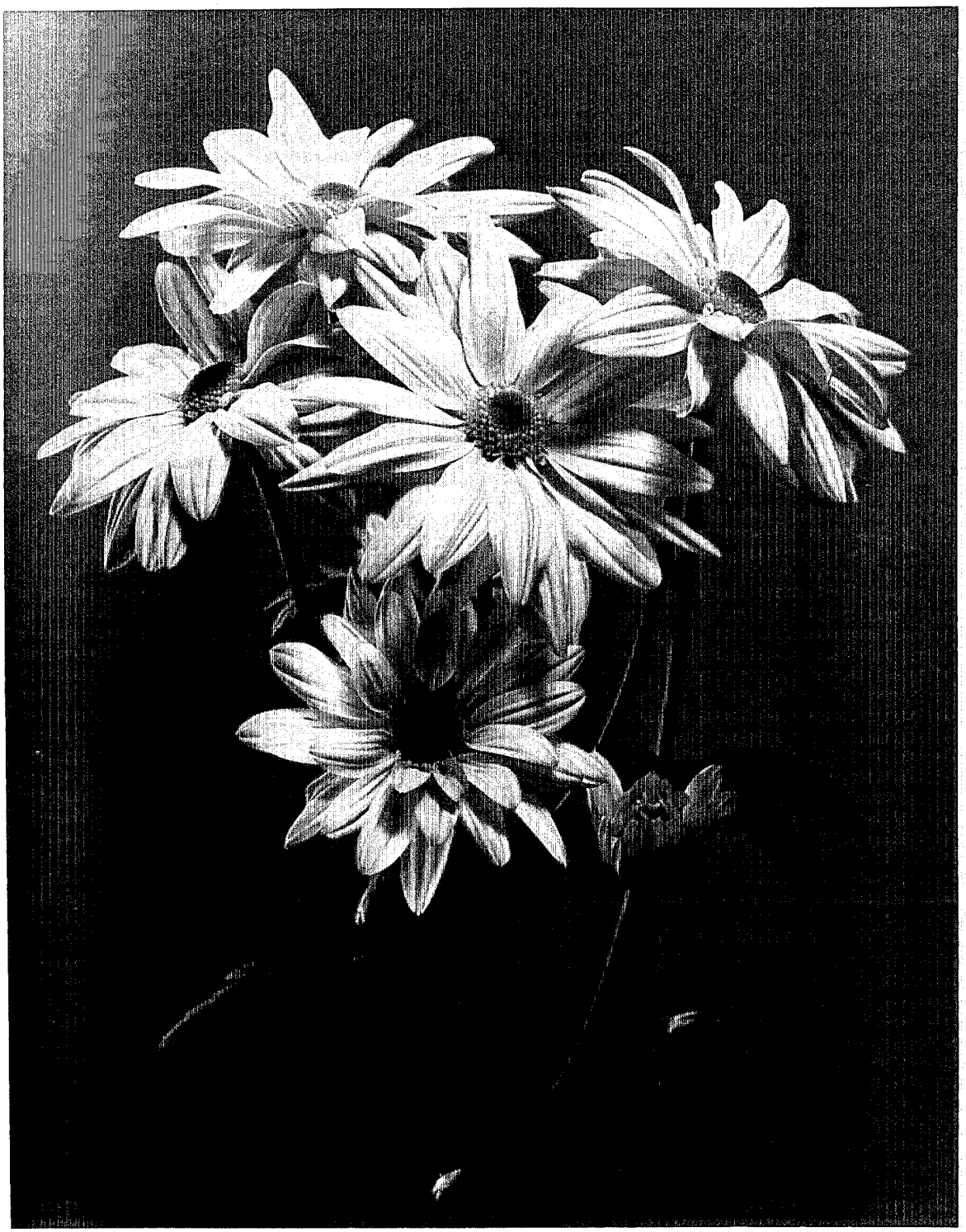

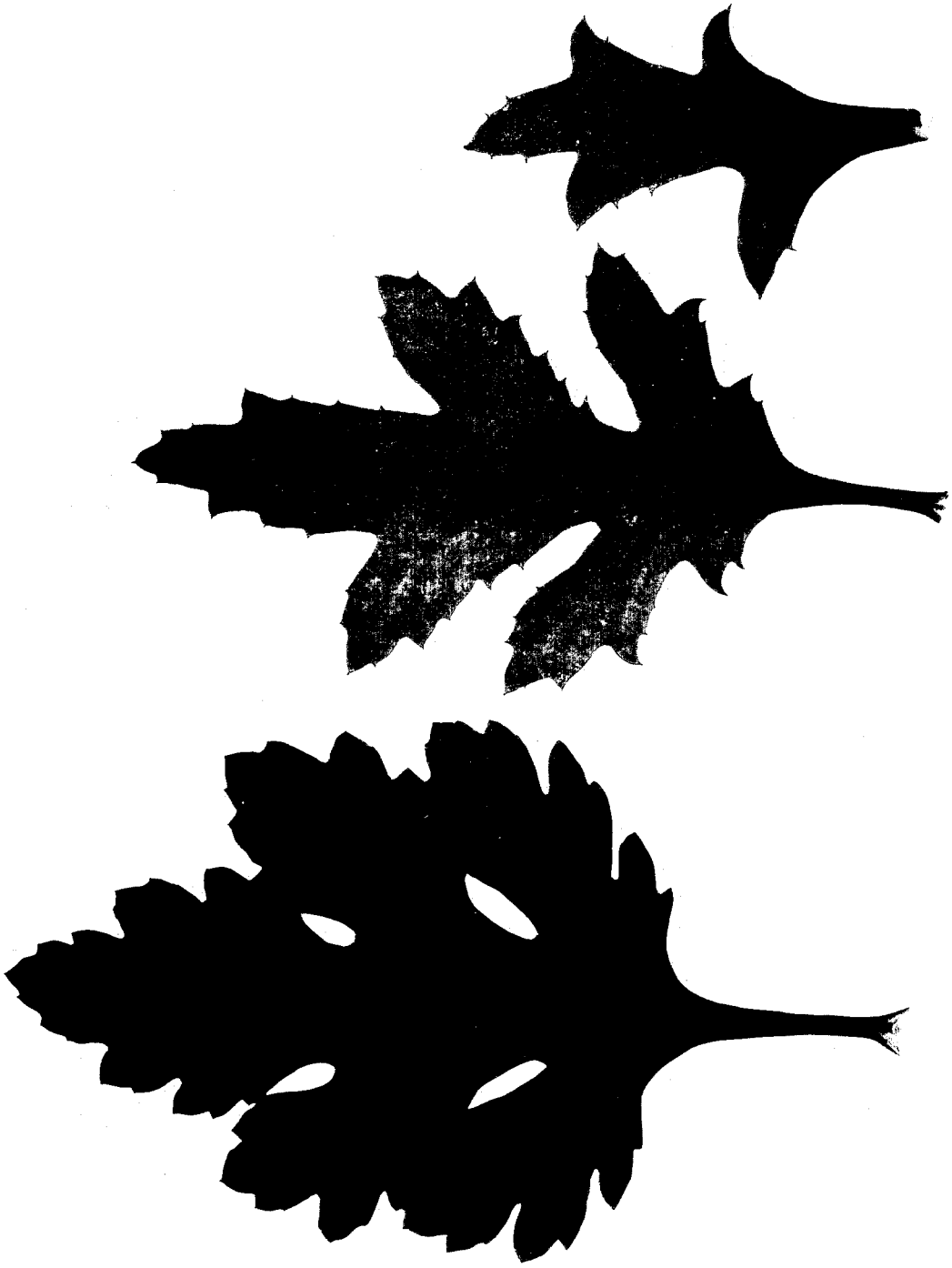

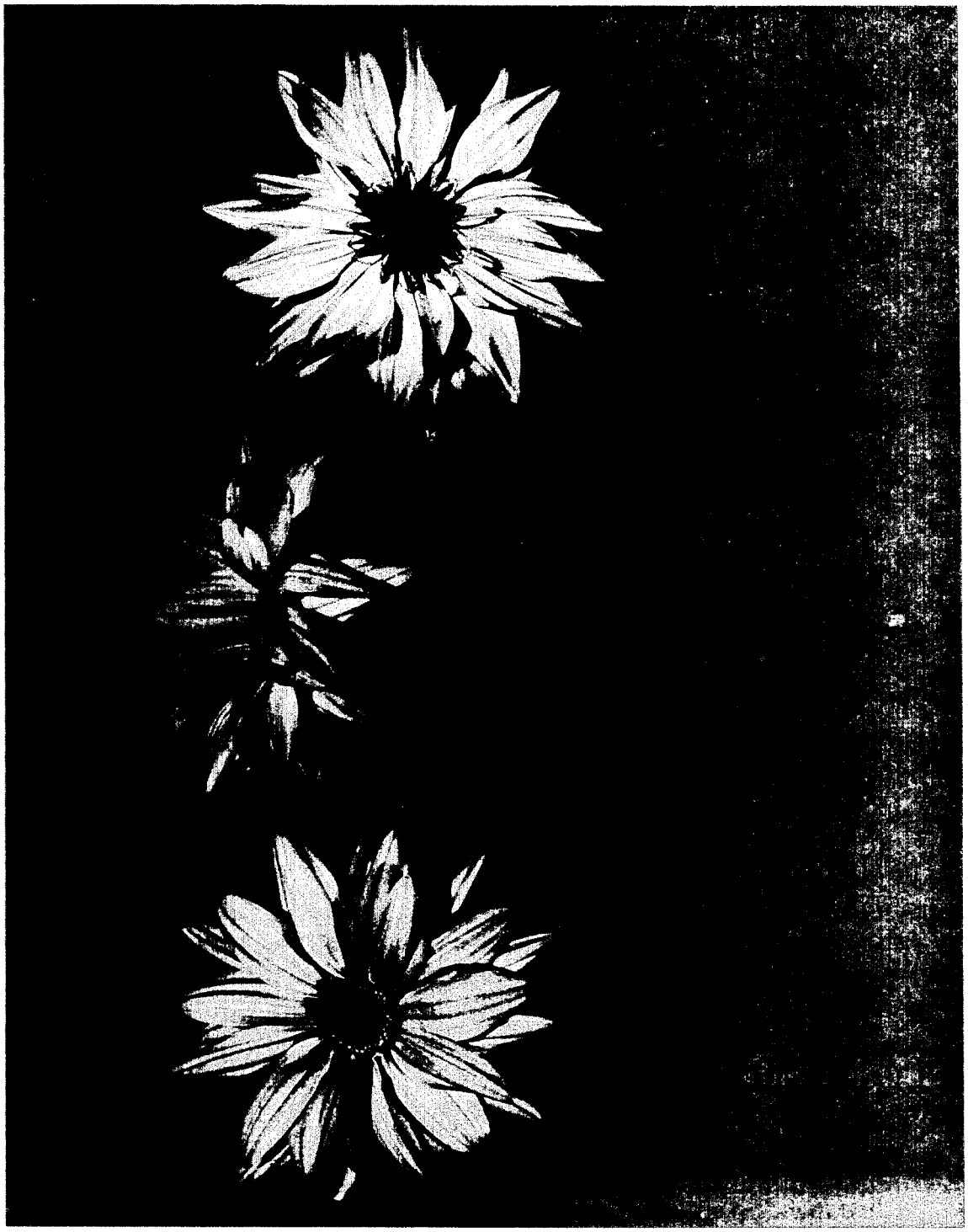

* * * * *